United States Patent
Sogabe et al.

(10) Patent No.: US 7,429,633 B2
(45) Date of Patent: Sep. 30, 2008

(54) BRUSH-FORM ALTERNATIVE COPOLYMER AND PROCESS FOR PRODUCING THE SAME

(75) Inventors: Atsushi Sogabe, Yokohama (JP); Isamu Kaneda, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 190 days.

(21) Appl. No.: 10/592,727

(22) PCT Filed: Apr. 5, 2005

(86) PCT No.: PCT/JP2005/006664

§ 371 (c)(1),
(2), (4) Date: Sep. 14, 2006

(87) PCT Pub. No.: WO2005/097857

PCT Pub. Date: Oct. 20, 2005

(65) Prior Publication Data

US 2007/0203303 A1    Aug. 30, 2007

(30) Foreign Application Priority Data

Apr. 9, 2004    (JP)    ............................... 2004-115714

(51) Int. Cl.
*C08L 33/12*    (2006.01)
*C08L 55/00*    (2006.01)

(52) U.S. Cl. ........................ 525/910; 525/911; 526/72
(58) Field of Classification Search ................ 525/910, 525/611; 526/72
See application file for complete search history.

(56) References Cited

U.S. PATENT DOCUMENTS

| 6,103,837 A * | 8/2000 | Hiiro et al. ................... 525/464 |
| 6,677,422 B2 * | 1/2004 | Coca et al. ............... 526/348.7 |
| 6,686,432 B2 * | 2/2004 | Coca et al. ............... 526/348.7 |

* cited by examiner

*Primary Examiner*—Elvis O Price
(74) *Attorney, Agent, or Firm*—Townsend & Banta

(57) ABSTRACT

The invention is an alternating copolymer, and a method of producing the same, obtained by alternately copolymerizing a vinylbenzyl-terminated polyethylene oxide (or polydimethylsiloxane) and a (meth)acryloyl-terminated polydimethylsiloxane (or polyethylene oxide).

The alternating copolymer is a novel amphiphilic brush-shaped alternating copolymer having a structure that is well-suited as an emulsifier or a dispersant for oil and silicone solvents commonly used in cosmetics and pharmaceuticals.

8 Claims, 4 Drawing Sheets

[FIG. 1]
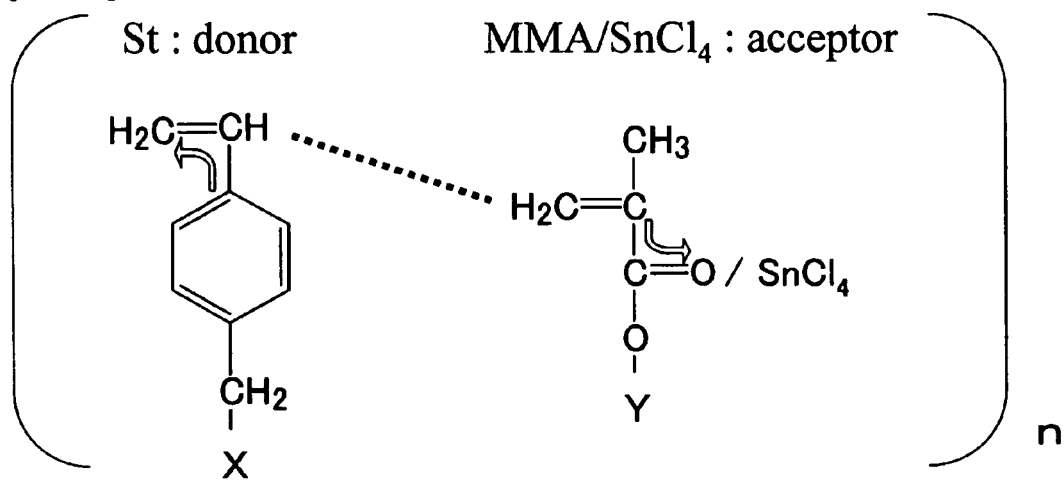
[FIG. 2]
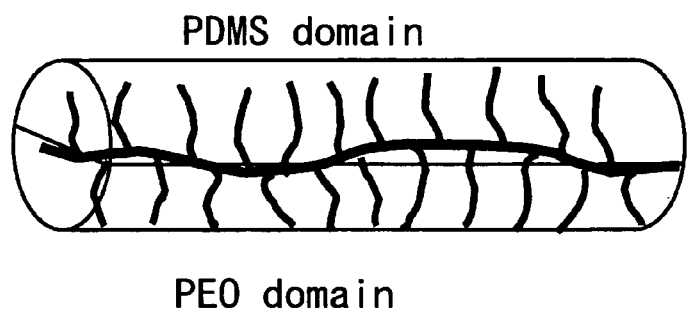
[FIG. 3]
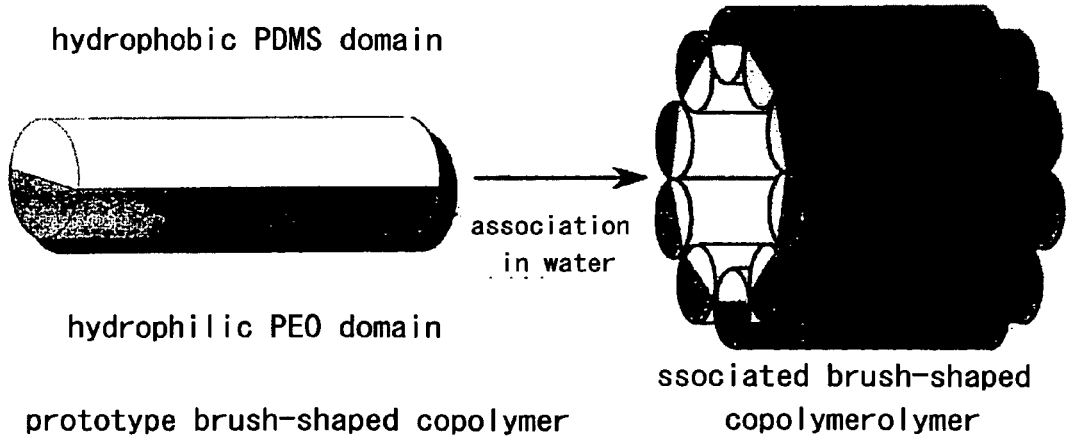

[FIG. 4]
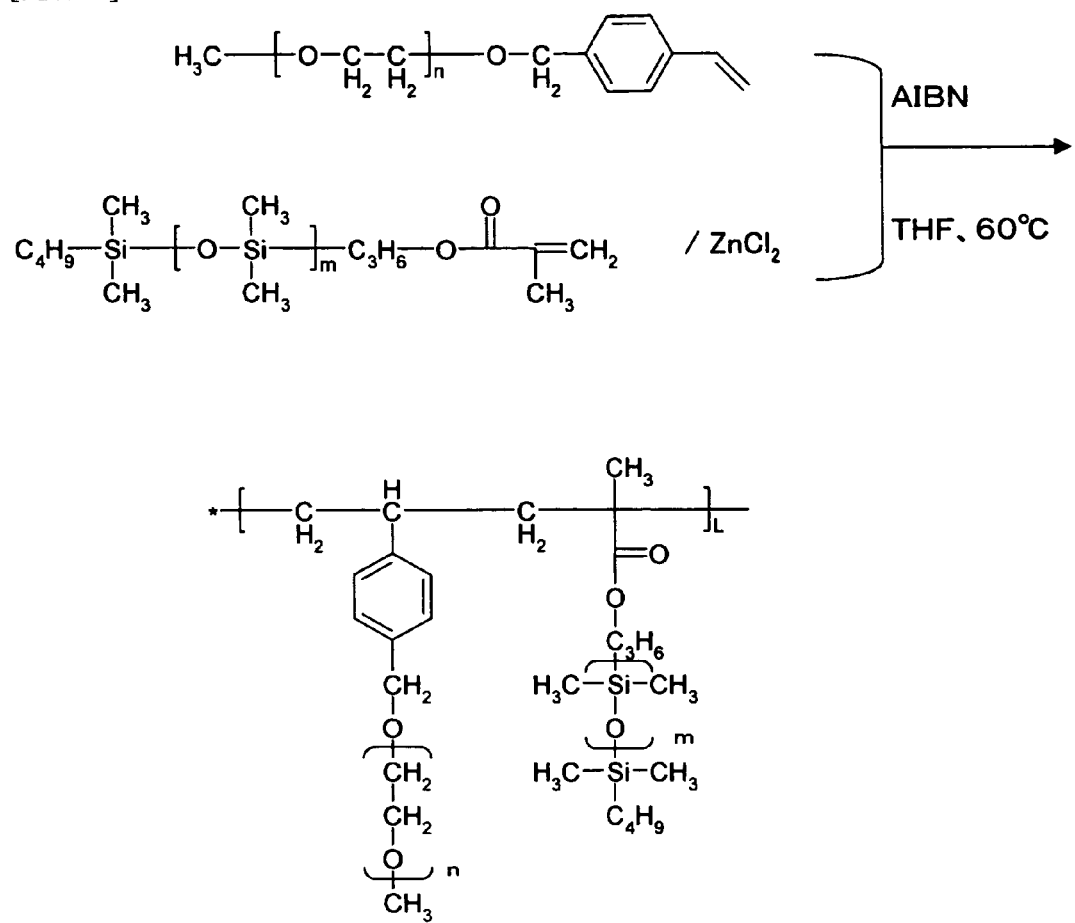

[FIG. 5]
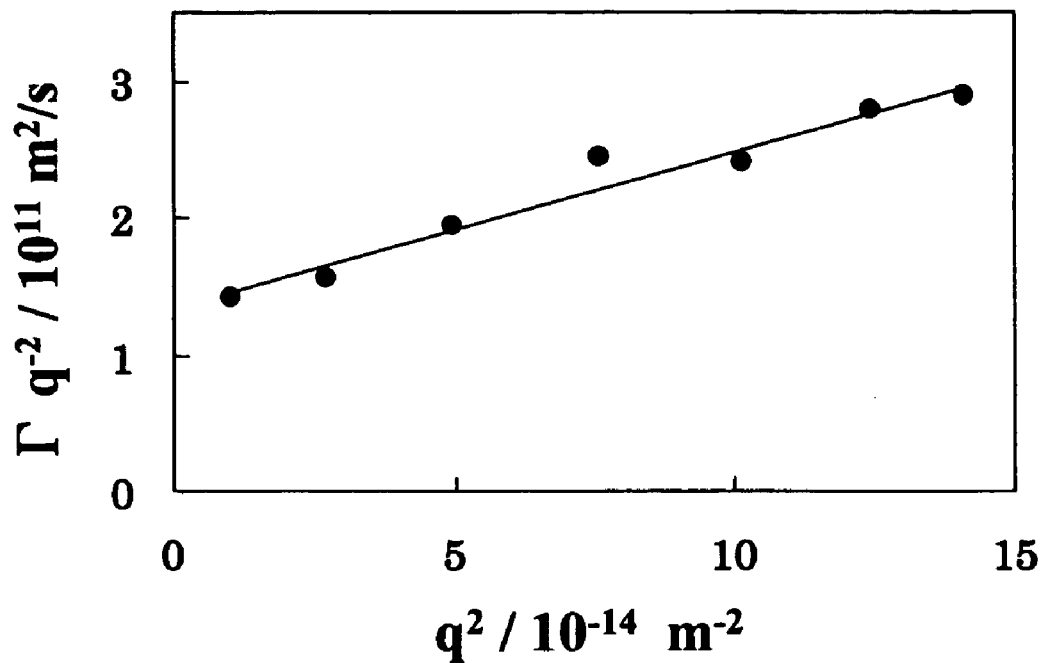
[FIG. 6]
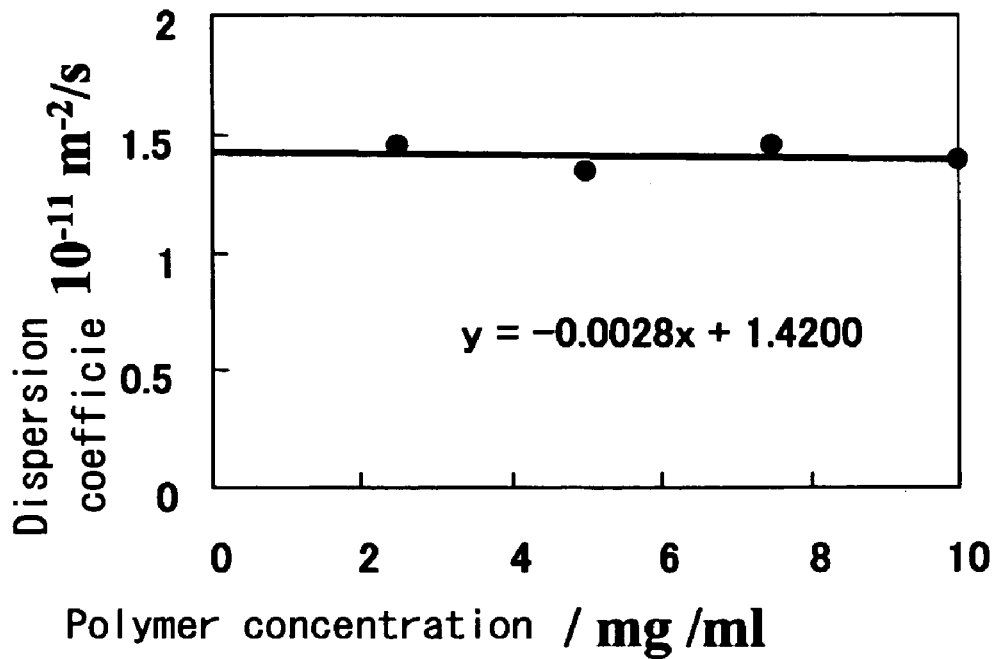

[FIG. 7]
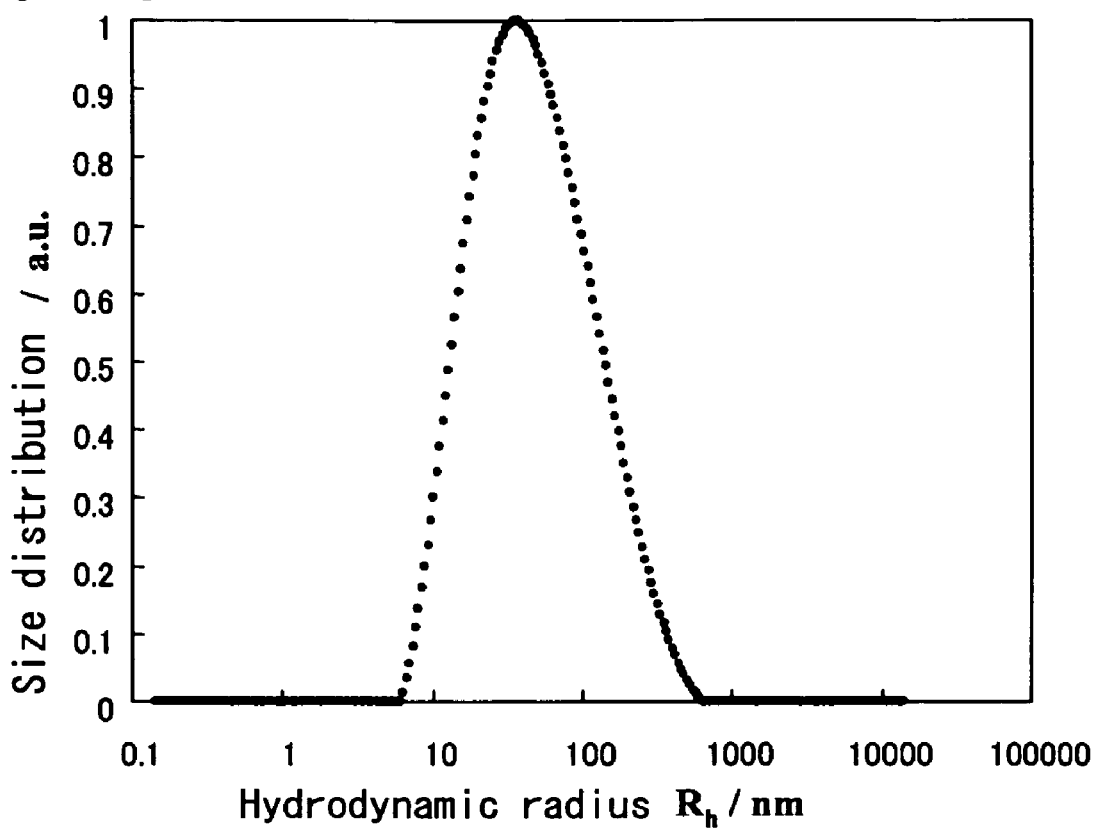
[FIG. 8]
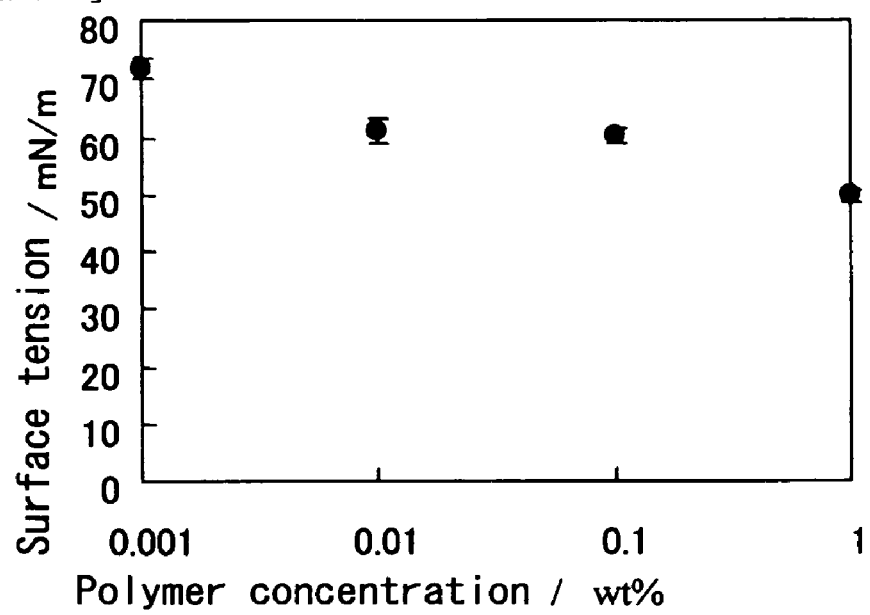

BRUSH-FORM ALTERNATIVE COPOLYMER AND PROCESS FOR PRODUCING THE SAME

This application is a 371 of PCT/JP05/06664, filed Apr. 5, 2005, which claims benefit to foreign application JP 2004-115714, filed Apr. 9, 2004.

TECHNICAL FIELD

The present invention relates to novel alternating copolymers and methods for producing the same. More specifically, it relates to amphiphilic alternating copolymers made of a hydrophilic macromonomer and a hydrophobic macromonomer, which, by exhibiting the function of providing a strong, stable adsorption film on an interface, can take on a brush-shaped structure that can find application as an emulsifier, dispersant, capsule, or coating agent, for example.

BACKGROUND ART

Amphiphilic polymers are one example of the polymers used in emulsifying agents, dispersing agents, capsules, and coating agents, for example. As the general structure of an amphiphilic polymer, there are random copolymers and block copolymers.

In random copolymers, the arrangement of the hydrophilic monomers and the hydrophobic monomers is not controlled, leading to a polymer chain that has poor efficiency at adsorbing to interfaces. In contrast, in block copolymers the hydrophilic monomers and hydrophobic monomers are arranged in a systematic manner and thus the polymer chain has an excellent ability to adsorb to interfaces. However, the large molecular weight of each segment does not allow the polymer chain to adhere closely, and as a result, satisfactory adsorption cannot be obtained.

In view of these matters, a brush-shaped amphiphilic alternating copolymer made of a vinylbenzyl-terminated polystyrene and a methacryloyl-terminated polyethylene oxide has been developed (see non-patent document 1 and non-patent document 2). This was arrived at by examining the various conditions for copolymerizing a vinylbenzyl-terminated polystyrene (PS-VB) with a methacryloyl-terminated polyethylene oxide (PEO-MC), and it was found that adding $SnCl_4$ to this copolymer system resulted in the formation of a $PEO-MC/SnCl_4$ complex that can be copolymerized with the PS-VB to obtain an alternating copolymer. In this alternating copolymer, a one-to-one charge transfer complex in which the PS-VB is the donor and the $PEO-MC/SnCl_4$ complex is the acceptor is formed, and it is thought that a homopolymer of the one-to-one charge transfer complex of these two is occurring. The amphiphilic alternating copolymer made of PS-VB and PEO-MC has side chains off a main chain that are high-density and incompatible with one another, and takes on a brush-shaped structure with a high aspect ratio. Further, the amphiphilic side chains are oriented alternately at the interface and thus the structure has excellent adsorption ability and adsorption density.

Non-Patent Document 1: K. Ishizu, X. X. Shen and K Tsubaki, *Polymer*, 41 2053(2000)

Non-Patent Document 2: K. Tsubaki, H. Kobayashi, J. Satoh and K. Ishizu, *J. Colloid Interface Sci.*, 241, 275(2001)

DISCLOSURE OF INVENTION

[Problem that the Present Invention Aims to Solve]

However, although the above brush-shaped alternating copolymer having alternating polystyrene and polyethylene oxide side chains has excellent ability to emulsify and disperse in an organic solvent dispersion medium, it is difficult to use it in the oils and silicone solvents commonly used in cosmetics and pharmaceuticals, for example.

The inventors have performed earnest investigations in order to produce a novel brush-shaped alternating copolymer that can be emulsified with and dispersed in the oils and silicone solvents commonly used in cosmetics and pharmaceuticals, and through their efforts successfully synthesized an amphiphilic brush-shaped alternating copolymer having alternating side chains polyethylene oxide and polypropylene oxide, and have already filed a patent application for this (Patent Application 2003-145648).

Although this amphiphilic brush-shaped alternating copolymer having alternating side chains of polyethylene oxide and polypropylene oxide can be used in oils commonly found in cosmetics and pharmaceuticals, for example, it did not demonstrate sufficient ability to emulsify or disperse in silicone solvents.

Accordingly, in light of the foregoing matters, the present inventors performed earnest investigations in order to obtain a novel brush-shaped alternating copolymer that can be emulsified with and dispersed in silicone solvents and the oils commonly used in cosmetics and pharmaceuticals, and successfully synthesized an amphiphilic brush-shaped alternating copolymer having alternating side chains of polyethylene oxide and polydimethylsiloxane, thus arriving at the present invention.

It is an object of the invention to provide a novel amphiphilic brush-shaped alternating copolymer whose structure makes it a good emulsifier and dispersant in oil and silicone solvents that are common in cosmetics and pharmaceuticals.

[Means to Solve the Problem]

In other words, the invention provides an alternating copolymer obtained by alternately copolymerizing a vinylbenzyl-terminated polyethylene oxide (or polydimethylsiloxane) and a (meth)acryloyl-terminated polydimethylsiloxane (or polyethylene oxide).

The invention also provides an alternating copolymer having the following repeating unit (1):

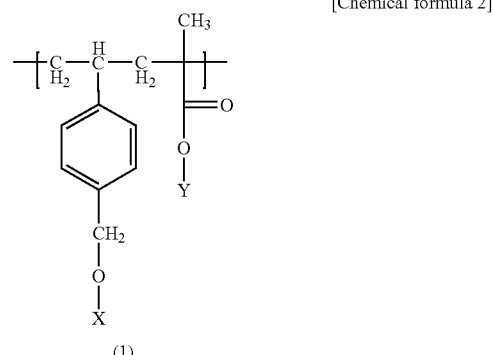

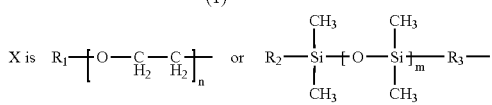

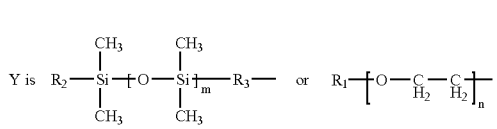

wherein m and n are numbers from 1 to 100, $R_1$ and $R_2$ can be identical or different, each independently representing a hydrogen or a straight chain or a branched alkyl group having 1 to 13 carbon atoms, and $R_3$ is a straight chain or a branched alkylene group having 1 to 13 carbons.

The invention also provides the above alternating copolymer in which the weight-average molecular weight of the alternating copolymer is 100,000 to 10,000,000.

The invention provides a method of producing the above alternating copolymer, in which a (meth)acryloyl-terminated polyethylene oxide (or polydimethylsiloxane) forms a charge transfer complex with a Lewis acid, a one-on-one complex is formed with a vinylbenzyl-terminated polydimethylsiloxane (or polyethylene oxide), and in the presence of an initiator the two are radically polymerized in a solvent.

The invention also provides the above method of producing an alternating copolymer, characterized in that the Lewis acid is $SnCl_4$ or $ZnCl_2$.

[Effects of the Invention]

The alternating copolymer of the invention is a novel amphiphilic alternating copolymer having alternating side chains of polyethylene oxide and polydimethylsiloxane. The alternating copolymer of the invention is an amphiphilic alternating copolymer having alternating (every other carbon of the main chain) side chains of polyethylene oxide and polydimethylsiloxane on a main chain whose basic backbone is an alternating copolymer of styrene and MMA. Thus, it is easy to form a rigid cylindrical structure (rod) having hydrophilic and hydrophobic graft side chains at a high-density. Further, an alternating copolymer whose weight-average molecular weight is 100,000 to 10,000,000 is polymerized with ease, and from the standpoint of the degree of polymerization as well, it is easy to form a brush-shaped structure.

The main chain of the alternating copolymer of the invention has polymer side chains at high-density that are not compatible with each other, and takes the form of a brush-shaped structure with a high aspect ratio. Consequently, the alternating copolymer of the invention demonstrates function as a surfactant such as an emulsifier or a dispersant. Further, since it forms a several-micron rod-shaped association in an appropriate solvent, it also can be employed as a capsule. Additionally, the rigid cylindrical structure (rod) that it forms can function as a thickener in addition to association properties. Its side chains are polyethylene oxide and polydimethylsiloxane, and this makes it suited for dissolving into general cosmetic oils such as silicone oils.

BRIEF DESCRIPTION OF DRAWINGS

FIG. 1 is a schematic of the complex made from PEO-VB and Si-MC.

FIG. 2 is a schematic of the brush-shaped structure that can be assumed by the amphiphilic alternating copolymer of the invention.

FIG. 3 is a schematic of the rod-shaped association in which the brush-shaped alternating copolymer has associated.

FIG. 4 is a reaction scheme of Example 1.

FIG. 5 shows the $\Gamma_e q^2$ with respect to the scattering vector $q^2$ of the AL1 obtained in Example 1.

FIG. 6 shows the translational diffusion coefficient $D(C)$ with respect to the concentration in benzene of the AL1 obtained in Example 1.

FIG. 7 shows the size distribution in water of the AL1 obtained in Example 1, obtained by dynamic light scattering measurement.

FIG. 8 shows the change in surface tension with respect to the concentration of the AL1 obtained in Example 1.

BEST MODE FOR CARRYING OUT THE INVENTION

The present invention is described in detail below.

In general, a brush-shaped polymer means a polymer in which a main chain having graft side chains at high-density is extended in the main axis direction due to the excluded volume effect of the side chains in both solvents, forming a rigid cylindrical structure.

In particular, using macromonomers as the monomers facilitates the formation of a cylindrical structure because macromonomers are expected to provide high density and a large excluded volume effect. The molecular weight of the polymer is related to its structure, and when the polymer has a small degree of polymerization it does not become cylindrical and instead becomes spherical or a rugby ball-shaped oval shape, and thus a large degree of polymerization is necessary if the polymer is to take on a brush shape.

The alternating copolymer of the invention is an amphiphilic alternating copolymer that has alternating (every other carbon of the main chain) side chains of polyethylene oxide and polydimethylsiloxane off of a main chain whose basic backbone is an alternating copolymer of styrene and MMA. Consequently, the hydrophilic and hydrophobic graft side chains are present at very high density, and this polymer may be called a brush-shaped copolymer and easily forms a rigid cylindrical structure (rod). It is easy to polymerize an alternating copolymer whose weight-average molecular weight is between 100,000 to 10,000,000, and thus from the standpoint of the degree of polymerization as well, it is easy to form a brush-shaped structure.

In this invention, the vinylbenzyl-terminated polyethylene oxide (or polydimethylsiloxane) (hereinafter abbreviated PEO-VB) is a vinylbenzyl vinyl monomer whose basic structure has the following formula (2). Here, vinylbenzyl-terminated polyethylene oxide (or polydimethylsiloxane) is used to mean both a vinylbenzyl-terminated polyethylene oxide and a vinylbenzyl-terminated polydimethylsiloxane.

As long is the alternating copolymer of the invention may be polymerized, the carbons in formula (2) can be replaced by any substituent group.

[Chemical formula 3]

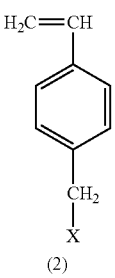

(2)

X is a side chain made of polyethylene oxide or polydimethylsiloxane) whose degree of polymerization and terminal structure are not restricted. For example, it may be made of polyethylene oxide (or polydimethylsiloxane) whose degree of polymerization is 1 to 100 and which has OH and alkyl ether terminals.

Preferably the PEO-VB is a macromonomer whose degree of polymerization is between 20 and 100.

Preferably X is the following.

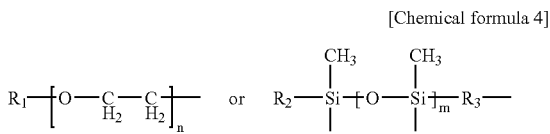

[Chemical formula 4]

wherein m and n are numbers from 1 to 100, $R_1$ and $R_2$ can be identical or different, each independently representing a hydrogen or a straight chain or a branched alkyl group having 1 to 13 carbon atoms, and $R_3$ is a straight chain or a branched alkylene group having 1 to 13 carbons.

Although $R_1$, $R_2$, and $R_3$ are not important factors in the copolymer of the invention, the $R_1$ and $R_2$ (alkyl group) terminals preferably are methyl, ethyl, butyl, or propyl groups. $R_3$ (alkylene group) preferably is methylene, ethylene, propylene, or butylene.

The PEO-VB is obtained by alkoxylating a commercially available polyethylene glycol monoalkyl ether of any molecular weight, or polydimethylsiloxane having a single terminal OH, with NaH in toluene, and then reacting this with a commercially available p-chloromethylstyrene by an ordinary method. Specifically, a commercially available polyethylene glycol monoalkyl ether of any molecular weight is freeze dried in benzene, dehydrated THF solvent is added thereto in a nitrogen atmosphere and then five parts NaH are added to carry out alkoxylation, then to this polyethylene glycol monomethyl ether/THF solution are added two parts p-chloromethylstyrene and the reaction is carried out. The sodium salt that is produced is filtered out and this filtrate is concentrated by evaporation, and benzene is added. This is then purified by filtering out the sodium salt that is produced and adding hexane dropwise to this filtrate to precipitate the polymer. It should be noted that the alkyl terminal of the commercially available polyethylene glycol monoalkyl ether is for example a methyl, lauryl, oleyl, or myristyl group. Any PEO-VB can be obtained by producing a polyethylene glycol monoalkyl ether of any molecular weight having an alkyl terminal, or a polydimethylsiloxane having a single terminal OH, by an ordinary method.

The (meth)acryloyl-terminated polydimethylsiloxane (or polyethylene oxide) of the invention is a (meth)acrylic vinyl monomer whose basic structure is shown below in formula (3).

In the invention, (meth)acryloyl-terminated polydimethylsiloxane (or polyethylene oxide) (abbreviated as Si-MC) is used to mean a (meth)acryloyl-terminated polydimethylsiloxane or a (meth)acryloyl-terminated polyethylene oxide. However, it means a (meth)acryloyl-terminated polydimethylsiloxane if the PEO-VB is a vinylbenzyl-terminated polyethylene oxide, and means a (meth)acryloyl-terminated polyethylene oxide if the PEO-VB is a vinylbenzyl-terminated polydimethylsiloxane.

(Meth)acrylic means methacrylic or acrylic, and in the case of acrylic the methyl in formula (3) is a hydrogen. The methacrylic form is preferable.

As long is the alternating copolymer of the invention may be polymerized, the carbons in formula (3) can be replaced by any substituent group.

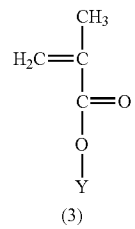

[Chemical formula 5]

(3)

Y is a side chain made of polydimethylsiloxane (or polyethylene oxide) whose degree of polymerization and terminal structure are not restricted. For example, it may be made of polyethylene oxide (or polydimethylsiloxane) whose degree of polymerization is 1 to 100 and which has OH and alkyl ether terminals.

Preferably the Si-MC is a macromonomer whose degree of polymerization is between 20 and 100.

Preferably Y is the following.

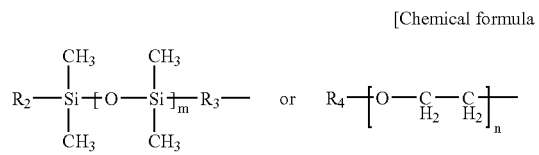

[Chemical formula 6]

wherein m and n are numbers from 1 to 100, $R_1$ and $R_2$ can be identical or different, each independently representing a hydrogen or a straight chain or a branched alkyl group having 1 to 13 carbon atoms, and $R_3$ is a straight chain or a branched alkylene group having 1 to 13 carbons.

Although $R_1$, $R_2$, and $R_3$ are not important factors in the copolymer of the invention, the $R_1$ and $R_2$ (alkyl group) terminals preferably are methyl, ethyl, butyl, or propyl groups. $R_3$ (alkylene group) preferably is methylene, ethylene, propylene, or butylene.

It should be noted that it is not necessary for these to be identical to the $R_1$, $R_2$, and $R_3$ in the X moiety of the PEO-VB.

The Si-MC is obtained by reacting a commercially available polydimethylsiloxane, or a polyethylene glycol monoalkyl ether, of any molecular weight and having a single terminal OH, with methacryloyl chloride (or acryloyl chloride) in THF by an ordinary method using triethylamine as an additive agent. Specifically, to a commercially available polydimethylsiloxane of any molecular weight and having a single terminal OH was added, in a vacuum, to dehydrated THF solvent, five parts methacryloyl chloride were added, then triethylamine was added as an additive and these were reacted. The product was precipitated in hexane and dried, then once again dissolved in THF, precipitated in hexane and dried to purify it. Any Si-MC may be obtained by producing a polyethylene glycol monoalkyl ether of any molecular weight having an alkyl terminal, or a polydimethylsiloxane having a single terminal OH, by an ordinary method.

In the amphiphilic alternating copolymer of the invention it is necessary to add a Lewis acid in order to cause the PEO-VB to function as the acceptor of a charge-transfer complex. The Lewis acid complexes with the ester moiety of the (meth) acrylate and lowers the electron density of the vinyl portion. This enhances its role as an acceptor. In the invention, it is particularly preferable that $SnCl_4$ or $ZnCl_2$ is used. The PEO-VB functions as a donor and forms a complex with the Si- MC/Lewis acid and polymerization proceeds, producing an alternating copolymer of PEO-VB and Si-MC. FIG. 1 shows a schematic of this complex.

There are no particular limitations regarding the polymerization solvent, as long as the solvent does not hinder formation of the complex between the PEO-VB and the Si-MC/Lewis acid. For example, there are no particular limitations as long as formation of the complex between the macromonomer (2) and the Lewis acid, or formation of the complex between the macromonomer (1) and the macromonomer (2)/Lewis acid, is not hindered. For example, it is possible to use an aliphatic hydrocarbon such as n-hexane or n-heptane, a cyclic hydrocarbon such as cyclohexane or cyclopentane, an aromatic hydrocarbon such as benzene or toluene, or an ether compound such as tetrahydrofuran.

There are no particular limitations regarding the polymerization initiator as long as it is capable of starting radical polymerization. For example, it is possible to use free radical polymerization initiators such as azoisobutyronitrile and benzoyl peroxide, and in the case of living radical polymerization, possible examples include initiation seeds such as an N,N-diethyldithiocarbamate group, 1,1,2,2-tetraphenylethane derivatives, and halogenated alkyl groups.

The polymerization temperature is appropriately determined depending on the initiator of the radical polymerization. For example, if the initiator is for a free radical polymerization, then the polymerization is performed at a temperature near the 10-hour half life of the initiator. In the case of azoisobutyronitrile, polymerization is conducted at 40 to 80° C. If the initiator is a N,N-diethyldithiocarbamate group, which is an initiation seed for living-radical polymerization, then there are no particular limitations regarding the temperature because the radical is generated due to the irradiation of ultraviolet light. There also are no particular limitations regarding the polymerization temperature when the initiation seed is a halogenated alkyl and the radical is created by a metal complex. If the initiation seed is a 1,1,2,2-tetraphenylethane derivative, then polymerization is conducted between 50 and 150° C. because the radical is generated by heat.

The reaction vessel that is used is an ordinary reaction vessel used in a radical polymerization, but if a photo iniferter group such as a N,N-diethyldithiocarbamate group is used as the initiation seed, then a transparent vessel is used because ultraviolet radiation is used.

Prior to starting polymerization it is necessary to sufficiently remove oxygen within the reaction system, and it is necessary to replace the system with an inert gas such as nitrogen or argon.

Polymerization may require from one to about 200 hours, and the polymerization is conducted within this range of polymerization times.

As for stopping polymerization, if the radical is generated by heating, then the polymerization is stopped by removing the heat, and if the radical is generated by ultraviolet radiation, then the polymerization is stopped by removing the ultraviolet radiation. If the radical is generated by adding a metal complex, then removing the metal complex or inactivating the polymerization by introducing oxygen, for example, quickly stops the polymerization. Polymerization also stops when all of the monomers have been used up by the polymerization.

Purification of the polymer is performed in accordance with a general polymer purification method and carried out by precipitation with a poor solvent, dialysis, or by distilling the polymerization solvent.

The molecular weight of the alternating copolymer that is yielded through the above polymerization is from 100,000 to 10,000,000. This is adjusted by the amount of polymer initiator that is added, the monomer concentration, the polymerization time, and the polymerization temperature, for example.

It should be noted that the weight-average molecular weight is a value that is found through static light scattering measurement.

The preferable repeating unit making up the amphiphilic alternating copolymer of the invention that is obtained as above is shown in formula (1) below.

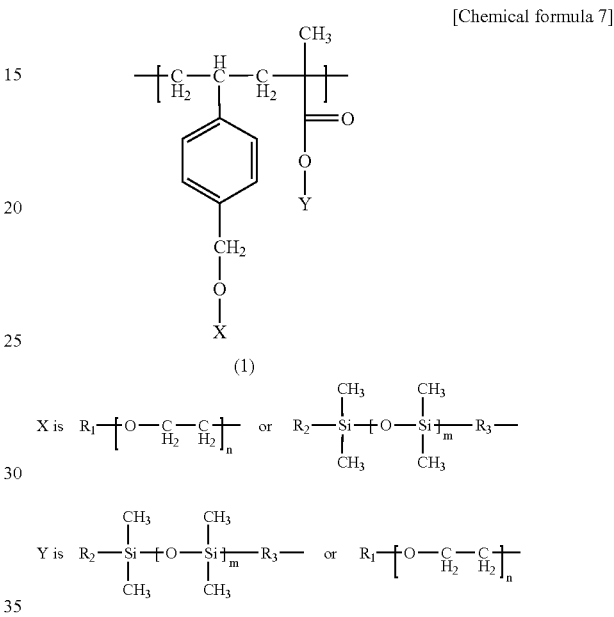

[Chemical formula 7]

wherein m and n are numbers from 1 to 100, $R_1$ and $R_2$ can be identical or different, each independently representing a hydrogen or a straight chain or a branched alkyl group having 1 to 13 carbon atoms, and $R_3$ is a straight chain or a branched alkylene group having 1 to 13 carbons.

As long as the properties of the amphiphilic alternating copolymer of the invention are not substantially inhibited, cases where a small amount of other general monomers are polymerized between the alternating units of PEO-VB and Si-MC or diads or triads of the PEO-VB or the Si-MC are present also fall within the range of equivalency of the alternating copolymer of the invention. There are no restrictions regarding the terminal ends of the main chain of the alternating copolymer.

The amphiphilic alternating copolymer of the invention has a brush-shaped structure with a high aspect ratio, in which the side chains off its main chain are high-density and not compatible with one another. Consequently, the alternating copolymer of the invention demonstrates function as a surfactant such as an emulsifier or a dispersant. Further, since it forms a several-micron rod-shaped association in an appropriate solvent, it also can be employed as a capsule. Additionally, the rigid cylindrical structure (rod) that it forms exhibits function as a thickener due to its association properties. Its side chains are polyethylene oxide and polydimethylsiloxane, and thus it is suited for dissolving into general oils such as cosmetic products. Consequently, as cosmetic raw material it can be favorably adopted as a surfactant, thickener, or coating agent, for example. Particularly preferable applications of the alternating copolymer of the invention include an amphiphilic high molecular weight surfactant, an amphiphilic high molecular weight dispersant, and an amphiphilic high molecular weight thickener.

FIG. 2 shows a schematic of the brush-shaped structure that can be taken by the amphiphilic alternating copolymer of the present invention. The lower half of the cylinder depicting the alternating copolymer represents the domain in which the high-density polyethylene oxide side chains, which are shown by the dashed line, are present. The upper half represents the domain in which the high-density polydimethylsiloxane side chains, which are expressed by the solid line, are present. The bold line in the middle having the polyethylene oxide side chains and the polydimethylsiloxane side chains indicates the main chain, which has a basic backbone of styrene and MMA.

FIG. 3 is a schematic of the rod-shaped association in which the brush-shaped alternating copolymer has associated.

EXAMPLES

The invention is described in specific detail through Examples, but the invention shall not be limited to these implementations.

The properties of the brush-shaped alternating copolymer that was obtained were measured through the following methods.

Molecular Weight and Molecular Weight Distribution

Using the DLS7000 made by Otsuka Electronics Co. Ltd., static light scattering measurement was performed with an Ar laser (wavelength 488 mm), in benzene at 25° C. Using a Zimm-plot, the weight-average molecular weight Mw and the radius gyration Rg were calculated. The degree of polymerization $(DP)_A$ was calculated from the overall molecular weight, taking the silicone/PEO alternating unit as one unit.

The high performance liquid chromatograph HLC-8120 made by Toso was used as a GPC. For the column, two TSK gel columns $GMH_{XL}$ and $G2000H_{XL}$ were used, THF was the solvent, and the measurement temperature was 40° C. The molecular weight distribution was calculated from the GPC profile.

Polymer Size

Using the DLS7000 made by Otsuka Electronics Co. Ltd., dynamic light scattering measurement was performed with an Ar laser (wavelength 488 mm), in benzene at 25° C. The apparent diffusion coefficient from 30° C. to 150° C. was measured to find the translational diffusion coefficient by 0-degree extrapolation. Also, the hydrodynamic radius Rh was calculated from the Einstein-Stokes equation.

Composition Ratio of the Polymer

Using a 1H-NMR (made by JEOL; GSX-500NMR spectrometer), the unit ratio of the PEO-VB and the Si-MC in the polymer was calculated from the area ratio of the methylene group (3.5 ppm) of the polyethylene oxide part of the PEO-VB and the methyl group (0 ppm) of the dimethylsiloxane of Si-Mc.

Sample 1: Si-MC

As the Si-MC, the macromonomer FM-0711 made by Chisso Corporation was used as received. Its molecular weight was 1000.

It should be noted that the terminal alkyl group of the polydimethylsiloxane side chain is an n-butyl group, and the alkylene group is propylene.

Synthesis Example 1: PEO-VB

As for the PEO-VB, a commercially available polyethylene glycol monomethyl ether (Mn=2000, 30 g) was freeze dried in benzene, dehydrated THF solvent was added thereto in a vacuum, and then sodium hydride (0.64 g) was added to cause alkoxylation, after which vacuum distilled p-methylchloromethyl styrene (3.90 g) was added to carry out the reaction. After reacting, the solvent was removed by evaporation. Benzene was added and the subsequent salt was filtered out, then the filtrate was concentrated again and hexane was added thereto to precipitate the polymer. The action of filtering out the polymer, dissolving it in benzene and then precipitating it with hexane was performed two times to purify the polymer. The yield was 29.8 g. The number-average molecular weight calculated from the 1H-NMR was 2000.

Example 1

In a transparent reaction vessel the above PEO-VB (30 g) was dissolved in benzene (15 mL) and freeze dried. To this was added Si-MC (13.2 g), then THF (45 mL) was added and the mixture was agitated to dissolve the macromonomer. Next, $ZnCl_2$ (3 g) dissolved in THF (20 mL) was added and this was agitated sufficiently. Next, azoisobutyronitrile (0.133 g) dissolved in THF (1.5 mL) was added. The product was then degassed and the reaction vessel was sealed. The reaction vessel was placed in a 60° C. constant temperature bath, and, while shaking, polymerization was allowed to occur for 120 hours.

After polymerization, the reaction solution was dialyzed using a dialysis film whose molecular weight fraction is 12,000 using THF as the solvent to remove the unreacted macromonomer and the $ZnCl_2$. The product was poured into a large quantity of hexane to precipitate the polymer, and the polymer was obtained. The unreacted PEO-VB was removed with copious amounts of water. The properties of the copolymer that was obtained (abbreviated AL1) are shown in Table 1. This reaction scheme is shown in FIG. 4.

Example 2

In a transparent reaction vessel the above PEO-VB (30 g) was dissolved in benzene (15 mL) and freeze dried. To this was added Si-MC (13.2 g), then THF (90 mL) was added and the mixture was agitated to dissolve the macromonomer. Next, $ZnCl_2$ (3 g) dissolved in THF (40 mL) was added and this was agitated sufficiently. Next, azoisobutyronitrile (0.133 g) dissolved in THF (3 mL) was added. The product was then degassed and the reaction vessel was sealed. The reaction vessel was placed in a 60° C. constant temperature bath, and, while shaking, polymerization was allowed to occur for 120 hours.

After polymerization, the reaction solution was dialyzed using a dialysis film whose molecular weight fraction is 12,000 using THF as the solvent to remove the unreacted macromonomer and the $ZnCl_2$. The product was poured into a large quantity of hexane to precipitate the polymer, and the polymer was obtained. The unreacted PEO-VB was removed with copious amounts of water. The properties of the copolymer that was obtained (abbreviated AL2) are shown in Table 1.

Example 3

In a transparent reaction vessel the above PEO-VB (30 g) was dissolved in benzene (15 mL) and freeze dried. To this was added Si-MC (13.2 g), then THF (45 mL) was added and the mixture was agitated to dissolve the macromonomer. Next, $ZnCl_2$ (3 g) dissolved in THF (20 mL) was added and this was agitated sufficiently. Next, azoisobutyronitrile (0.266 g) dissolved in THF (1.5 mL) was added. The product was then degassed and the reaction vessel was sealed. The reaction vessel was placed in a 60° C. constant temperature bath, and, while shaking, polymerization was allowed to occur for 120 hours.

After polymerization, the reaction solution was dialyzed using a dialysis film whose molecular weight fraction is 12,000 using THF as the solvent to remove the unreacted macromonomer and the $ZnCl_2$. The product was poured into a large quantity of hexane to precipitate the polymer, and the polymer was obtained. The unreacted PEO-VB was removed with copious amounts of water. The properties of the copolymer that was obtained (abbreviated AL3) are shown in Table 1.

Example 4

In a transparent reaction vessel the above PEO-VB (30 g) was dissolved in benzene (15 mL) and freeze dried. To this was added Si-MC (13.2 g), then THF (45 mL) was added and the mixture was agitated to dissolve the macromonomer. Next, $ZnCl_2$ (3 g) dissolved in THF (20 mL) was added and this was agitated sufficiently. Next, azoisobutyronitrile (0.399 g) dissolved in THF (1.5 mL) was added. The product was then degassed and the reaction vessel was sealed. The reaction vessel was placed in a 60° C. constant temperature bath, and, while shaking, polymerization was allowed to occur for 120 hours.

After polymerization, the reaction solution was dialyzed using a dialysis film whose molecular weight fraction is 12,000 using THF as the solvent to remove the unreacted macromonomer and the $ZnCl_2$. The product was poured into a large quantity of hexane to precipitate the polymer, and the polymer was obtained. The unreacted PEO-VB was removed with copious amounts of water. The properties of the copolymer that was obtained (abbreviated AL4) are shown in Table 1.

TABLE 1

| Sample name | $M_w$ (*1) | $M_w/M_n$ (*2) | $(DP)_A$ (*3) | $R_g$ (nm) (*1) | $R_h$ (nm) (*4) | $R_g/R_h$ |
|---|---|---|---|---|---|---|
| AL-1 | $2.78 \times 10^6$ | 1.60 | 927 | 48.5 | 23.5 | 2.06 |
| AL-2 | $1.16 \times 10^6$ | 1.55 | 387 | 19.3 | 10.2 | 1.89 |
| AL-3 | $6.33 \times 10^5$ | 1.76 | 213 | 11.2 | 6.9 | 1.62 |
| AL-4 | $5.96 \times 10^5$ | 1.60 | 202 | 10.1 | 4.5 | 2.24 |

*1: Measured by static light scattering measurement in benzene at 25° C.
*2: Measured by GPC at 40° C. in THF
*3: Degree of polymerization with the Si/PEO alternating unit serving as the unit; measured by 1H-NMR
*4: Measured by static light scattering measurement in benzene at 25° C.

FIG. 5 shows the $\Gamma_e q^2$ with respect to the scattering vector $q^2$ of AL1. The strong dependence on the angle suggests that AL1 exhibits anisotropy due to a brush-like rather than a spherical structure originating from short side chains and a long main chain.

FIG. 6 shows the translational diffusion coefficient D(C) with respect to the concentration of AL1 in benzene. In a range of concentration from 1 to 5 mg/mL, D(C) is a constant value. From this it can be understood that AL1 in this concentration range exists as a single molecule.

Table 1 shows the hydrodynamic radius Rh, which was found from the translational diffusion coefficient $D_0$ in benzene and through the Einstein-Stokes equation. The value of Rg/Rh has been said to be 0.775 if spherical and 2.0 if a rigid rod shape, and the AL1 value of 2.0 indicates that its shape is close to a rigid rod in a good solvent.

FIG. 7 shows the size distribution of AL1 in water, obtained by dynamic light scattering measurement. At a polymer concentration of 1 mg/mL the hydrodynamic radius Rh was 28.0 nm, and at a polymer concentration of 10 mg/mL the hydrodynamic radius Rh was 37.9 nm. In water, at a polymer concentration in the range of 0.1 to 10 mg/mL, the aqueous solution was cloudy but precipitation was not observed. This indicates that in this concentration range a stable association is formed.

FIG. 8 shows the surface tension with respect to the concentration of AL1. AL1 exhibits a low surface tension from a polymer concentration of 0.01%.

FIG. 9 shows the emulsion ability of AL1. AL1 is capable of emulsifying silicone.

The above results show that an alternating copolymer of a vinylbenzyl-terminated polyethylene oxide and a methacryloyl-terminated polydimethylsiloxane was synthesized successfully, yielding a novel brush-shaped alternating copolymer.

INDUSTRIAL APPLICABILITY

The alternating copolymer of the invention is an amphiphilic alternating copolymer having alternating (every other carbon of the main chain) side chains of polyethylene oxide and polydimethylsiloxane on a main chain whose basic backbone is an alternating copolymer of styrene and MMA. Thus, it is easy to form a rigid cylindrical structure (rod) having hydrophilic and hydrophobic graft side chains at a high-density. Further, an alternating copolymer whose weight-average molecular weight is 10,000 to 10,000,000 is polymerized with ease, and from the standpoint of the degree of polymerization as well, it is easy to form a brush-shaped structure.

The main chain of the alternating copolymer has polymer side chains at high-density that are not compatible with each other, resulting in a brush-shaped structure with a high aspect ratio. Consequently, the alternating copolymer of the invention demonstrates function as a surfactant such as an emulsifier or a dispersant. Further, since it forms a several-micron rod-shaped association in an appropriate solvent, it also can be employed as a capsule. Additionally, the rigid cylindrical structure (rod) that it forms can function as a thickener in addition to association properties. Its side chains are polyethylene oxide and polydimethylsiloxane, and this makes it suited for dissolving into general cosmetic oils such as silicone oils. Consequently, it can find application in chemical products such as cosmetic products and adhesive agents as an emulsifier, dispersant, capsule, or coating agent, for example.

The invention claimed is:

1. An alternating copolymer obtained by alternately copolymerizing a vinylbenzyl-terminated polyethylene oxide (or polydimethylsiloxane) and a (meth)acryloyl-terminated polydimethylsiloxane (or polyethylene oxide).

2. An alternating copolymer having the following repeating unit (1):

[Chemical formula 1]

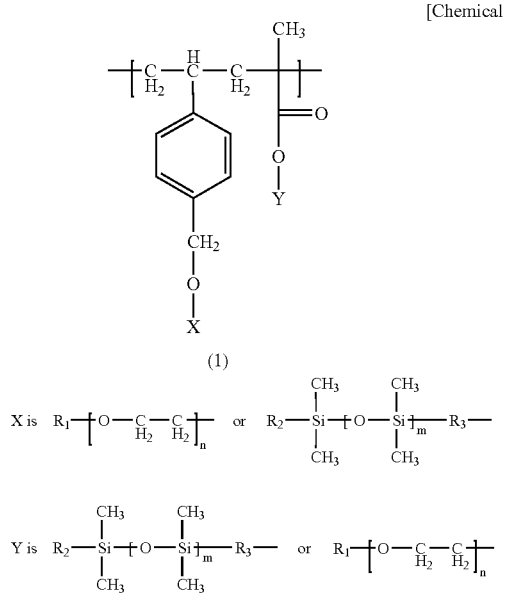

(1)

wherein m and n are numbers from 1 to 100, $R_1$ and $R_2$ can be identical or different, each independently representing a hydrogen or a straight chain or a branched alkyl group having 1 to 13 carbon atoms, and $R_3$ is a straight chain or a branched alkylene group having 1 to 13 carbons.

3. The alternating copolymer according to claim 1, wherein a weight-average molecular weight of the alternating copolymer is 100,000 to 10,000,000.

4. The method of producing an alternating copolymer according to claim 1, wherein a (meth)acryloyl-terminated polyethylene oxide (or polydimethylsiloxane) forms a charge transfer complex with a Lewis acid, a one-on-one complex is formed with a vinylbenzyl-terminated polydimethylsiloxane (or polyethylene oxide), and in the presence of an initiator the two are radically polymerized in a solvent.

5. The method of producing an alternating copolymer according to claim 4, wherein the Lewis acid is $SnCl_4$ or $ZnCl_2$.

6. The alternating copolymer according to claim 2, wherein a weight-average molecular weight of the alternating copolymer is 100,000 to 10,000,000.

7. The method of producing an alternating copolymer according to claim 2, wherein a (meth)acryloyl-terminated polyethylene oxide (or polydimethylsiloxane) forms a charge transfer complex with a Lewis acid, a one-on-one complex is formed with a vinylbenzyl-terminated polydimethylsiloxane (or polyethylene oxide), and in the presence of an initiator the two are radically polymerized in a solvent.

8. The method of producing an alternating copolymer according to claim 3, wherein a (meth)acryloyl-terminated polyethylene oxide (or polydimethylsiloxane) forms a charge transfer complex with a Lewis acid, a one-on-one complex is formed with a vinylbenzyl-terminated polydimethylsiloxane (or polyethylene oxide), and in the presence of an initiator the two are radically polymerized in a solvent.

* * * * *